United States Patent [19]
Auron et al.

[11] Patent Number: 5,821,053
[45] Date of Patent: Oct. 13, 1998

[54] LIL-STAT DNA BINDING SITES AND METHODS FOR IDENTIFYING INHIBITORY BINDING AGENTS

[75] Inventors: Philip E. Auron, Framingham; Junichi Tsukada, Brookline; Wayne R. Waterman, Watertown; Andrew C. Webb, Milton, all of Mass.

[73] Assignee: Center for Blood Research, Inc., Boston, Mass.

[21] Appl. No.: 386,728

[22] Filed: Feb. 10, 1995

[51] Int. Cl.⁶ .............................. C12Q 1/68; C07H 21/00; C07H 21/04
[52] U.S. Cl. .......................... 436/6; 435/172.3; 536/23.1; 536/24.1
[58] Field of Search .............................. 435/6, 69.1, 91.1, 435/172.1, 172.3, 325; 514/2, 44; 536/23.1, 24.5, 24.1

[56] References Cited

U.S. PATENT DOCUMENTS

5,464,938  11/1995  Smith et al. ............................. 530/350

OTHER PUBLICATIONS

Suzue, K., "Sequence of the Mouse Liver Glucose Transporter," Nucleic Acids Research, vol. 17, No. 23, p. 10099 (Nov. 1, 1989).

S. Ruff–Jamison et al., "Induction by EGF and Interferon–γ of Tyrosine Phosphorylated DNA Binding Proteins in Mouse Liver Nuclei", Science 261:1733–1736 (1993).

A.C. Larner et al., "Tyrosine Phosphorylation of DNA Binding Proteins by Multiple Cytokines", Science 261:1730–1733 (1993).

O. Silvennoiinen et al., "Ras–Independent Growth Factor Signaling by Transcription Factor Tyrosine Phosphorylation", Science 261:1736–1739 (1993).

H.B. Sadowski et al., "A Common Nuclear Signal Transduction Pathway Activated by Growth Factor and Cytokine Receptors", Science 261:1739–1744 (1993).

K. Shuai et al., "A Single Phosphotyrosine Residue of Stat91 Required for Gene Activation by Interferon–γ", Science 261:1744–1746 (1993).

C. Beadling et al., "Activation of JAK kinases and STAT proteins by interleukin–2 and interferon α, but not the T cell antigen receptor, in human T lymphocytes", The EMBO Journal 13(23):5605–5615 (1994).

S. Ruff–Jamison et al., "Epidermal Growth Factor and Lipopolysaccharide Activate Stat3 Transcription Factor in Mouse Liver", J. Bio. Chem. 269(35):21933–21935 (1994).

L.E. Reid et al., "A single DNA response element can confer inducibility by both α– and γ–interferons", Proc. Natl. Acad. Sci. USA 86:840–844 (1989).

F. Shirakawa et al., "The Human Prointerleukin 1β Gene Requires DNA Sequences Both Proximal and Distal to the Transcription Start Site for Tissue–Specific Induction", Molecular and Cellular Biology 13(3):1332–1334 (1993).

P.E. Auron and A.C. Webb, "Interleukin–1: a gene expression system regulated at multiple levels", Eur. Cytokine Netw. 5(6):573–592 (1994).

J. Tsukada et al., "Transcription Factors NF–IL6 and CREB Recognize a Common Essential Site in the Human Protinterleukin 1β Gene", Molecular and Cellular Biology, 14(11):7285–7297 (1994).

H. Wakao et al., "Mammary gland factor (MGF) is a novel member of the cytokine regulated transcription factor gene family and confers the prolactin response", The EMBO Journal, 13(9):2182–2191 (1994).

T. Matsuyama et al., "Targeted Disruption of IRF–1 or IRF–2 Results in Abnormal Type I IFN Gene Induction and Aberrant Lymphocyte Development", Cell 75:83–97 (1993).

J. Hou et al., "An Interleukin–4–Induced Transcription Factor: IL–4 Stat", Science 265:1701–1706 (1994).

Z. Zhong et al., "Stat3: A STAT Family Member Activated by Tyrosine Phosphorylation in Response to Epidermal Growth Factor and Interleukin–6", Science 264:95–98 (1994).

A.C. Greenlund et al., "Ligand–induced IFNγ receptor tyrosine phosphorylation couples the receptor to its signal transduction system (p91)", The EMBO Journal 13(7):1591–1600 (1994).

S. Akira et al., "Molecular Cloning of APRF, a Novel IFN–Stimulated Gene Factor 3 p91–Related Transcription Factor Involved in the gp130–Mediated Signaling Pathway", Cell 77:63–71 (1994).

Z. Zhong et al., "Stat3 and Stat4: Members of the family of signal transducers and activators of transcription", Proc. Natl. Acad. Sci. USA 91:4806–4810 (1994).

N. Tanaka et al., "Recognition DNA Sequences of Interferon Regulatory Factor 1 (IRF–1) and IRF–2, Regulators of Cell Growth and the Interferon System", Molecular and Cellular Biology 13(8):4531–4538 (1993).

K. Yamamoto et al., "Stat4, a Novel Gamma Interferon Activation Site–Binding Protein Expressed in Early Myeloid Differentiation", Molecular and Cellular Biology 14(7):4342–4349 (1994).

N. Stahl et al., "Association and Activation of Jak–Tyk Kinases by CNTF–LIF–OSM–IL–6 β Receptor Components", Science 263:92–95 (1994).

(List continued on next page.)

Primary Examiner—George C. Elliott
Assistant Examiner—Sean M. Garry
Attorney, Agent, or Firm—Helen Greer

[57] ABSTRACT

A method for finding an agent which inhibits interaction between LIL-Stat protein and a nucleic acid having a LIL-Stat binding sequence is described. The LIL-Stat protein is contacted with the nucleic acid in the presence of an agent which inhibits or does not inhibit the interaction between the LIL-Stat protein and the nucleic acid. It is determined whether or not the agent inhibits this interaction. Also described are a method for treating an inflammatory response in a mammal, a therapeutic inhibitory agent suitable for treating or preventing an inflammatory response in a mammal, and DNA molecules having a DNA sequence encoding a binding site for the LIL-Stat protein.

15 Claims, 3 Drawing Sheets

OTHER PUBLICATIONS

C. Lütticken et al., "Association of Transcription Factor APRF and Protein Kinase Jak1 with the Interleukin–6 Signal Transducer gp130", *Science* 263:89–92 (1994).

J.E. Darnell Jr. et al., "Jak–STAT Pathways and Transcriptional Activation in Response to IFNs and Other Extracellular Signaling Proteins", *Science* 264:1415–1421 (1994).

J.N. Ihle et al., "Signaling by the cytokine receptor superfamily: JAKs and STATs", *TIBS* 19:222–227 (1994).

C. Bovolenta et al., "Molecular interactions between interferon consensus sequence binding protein and members of the interferon regulatory factor family", *Proc. Natl. Acad. Sci. USA* 91:5046–5050 (1994).

W. Du et al., "Mechanisms of Transcriptional Synergism between Distinct Virus–Inducible Enhancer Elements", *Cell* 74:878–898 (1993).

K. Kuno et al., "Structure and Function of the Intracellular Portion of the Mouse Interleukin 1 Receptor (Type I)", *J. Biol. Chem.* 268(18):13510–13518 (1993).

S. Harroch et al., "Induction by interleukin–6 of interferon regulatory factor 1 (IRF–1) gene expression through the palindromic interferon response element pIRE and cell type–dependent control of IRF–1 binding to DNA", *The EMBO Journal* 13(8):1942–1949 (1994).

T. Improta et al., "Transcription factor ISGF–3 formation requires phosphorylated Stat912 protein, but Stat protein is phosphorylated independently of Stat91 protein", *Proc. Natl. Acad. Sci. USA* 91:4776–4780 (1994).

T. Fujita et al., "Induction of endogenous IFN–α and IFN–β genes by a regulatory transcription factor, IRF–1", *Nature* 337:270–272 (1989).

H. Harada et al., "Structurally Similar but Functionally Distinct Factors, IRF–1 and IRF–2, Bind to the Same Regulatory Elements of IFN and IFN–Inducible Genes", *Cell* 58:729–739 (1989).

A.D. Keller and T. Maniatis, "Identification of an inducible factor that binds to a positive regulatory element of the human β–interferon gene", *Proc. Natl. Acad. Sci. USA* 85:3309–3313 (1988).

M. Miyamoto et al., "Regulated Expression of a Gene Encoding a Nuclear Factor, IRF–1, That Specifically Binds to IFN–β Gene Regulatory Elements", *Cell* 54:903–913 (1988).

S. Goodbourn and T. Maniatis, "Overlapping positive and negative regulatory domains of the human β–interferon gene", *Proc. Natl. Acad. Sci. USA* 85:1447–1451 (1988).

C. Fan and T. Maniatis, "Two different virus–inducible elements are required for human β–interferon gene regulation", *The EMBO Journal* 8(1):101–110 (1989).

T. Fujita et al., "Interferon–β Gene Regulation: Tandemly Repeated Sequences of a Synthetic 6 bp Oligomer Function As a Virus–Inducible Enhancer", *Cell* 49:357–367 (1987).

S. Goodbourn et al., "The Human β–Interferon Gene Enhancer Is under Negative Control", *Cell* 45:601–610 (1986).

V.J. Palombella and T. Maniatis, "Inducible Processing of Interferon Regulatory Factor–2", *Molecular and Cellular Biology* 12(8):3325–3336 (1992).

X. Fu et al., "ISGF3, the transcriptional activator induced by interferon α, consists of multiple interacting polypeptide chains", *Proc. Natl. Acad. Sci. USA* 87:8555–8559 (1990).

X. Fu et al., "The proteins of ISGF–3, the interferon α–induced transcriptional activator, define a gene family involved in signal transduction", *Proc. Natl. Acad. Sci. USA* 89:7840–7843 (1992).

D.E. Levy et al., "Interferon–induced nuclear factors that bind a shared promoter element correlate with positive and negative transcriptional control", *Genes & Development* 2:383–393 (1988).

K. Shuai et al., "Interferon Activation of the Transcription Factor Stat91 Involves Dimerization through SH2–Phosphotyrosyl Peptide Interactions", *Cell* 76:821–828 (1994).

S.A. Veals et al., "Subunit of an Alpha–Interferon–Responsive Transcription Factor is Releated to Interferon Regulatory Factor and Myb Families of DNA–Binding Proteins", *Molecular and Cellular Biology* 12(8):3315–3324 (1992).

K. Shuai et al., "Activation of Transcription by IFN–γ: Tyrosine Phosphorylation of a 91–kD DNA Binding Protein", *Science* 258:1808–1812 (1992).

R.N. Pearse et al., "Interferon γ–induced transcription of the high–affinity Fc receptor of IgG requires assembly of a complex that includes the 91–kDa subunit of transcription factor ISGF3", *Proc. Natl. Acad. Sci. USA* 90:4314–4318 (1993).

C. Schindler et al., "Proteins of transcription factor ISGF–3: One gene encodes the 91– and 84–kDa ISGF–3 proteins that are activated by interferon α", *Proc. Natl. Acad. Sci. USA* 89:7836–7839 (1992).

D.S. Kessler et al., "Interferon–α regulates nuclear translocation and DNA–binding affinity of ISGF3, a multimeric transcriptional activator", *Genes & Development* 4:1753–1765 (1990).

C.J. Lowenstein et al., "Macrophage nitric oxide synthase gene: Two upstream regions mediate induction by interferon γ and lipopolysaccharide", *Proc. Natl. Acad. Sci. USA* 90:9730–9734 (1993).

Y. Ohmori and T.A. Hamilton, "Cooperative Interaction between Interferon (IFN) Stimulus Response Element and kB Sequence Motifs Controls IFNγ– and Lipopolysaccharide–stimulated Transcription from the Murine IP–10 Promoter", *Journal of Biological Chemistry* 268(9):6677–6688 (1993).

S.H. Sims et al., "A Novel Interferon–Inducible Domain: Structural and Functional Analysis of the Human Interferon Regulatory Factor 1 Gene Promoter", *Molecular and Cellular Biology* 13(1):690–702 (1993).

B.J. Wagner et al., "The SIF binding element confers sis/PDGF inducibility onto the c–fos promoter", *The EMBO Journal* 9(13):4477–4484 (1990).

R. Pine et al., "Purification and Cloning of Interferon–Stimulated Gene Factor 2 (ISGF2): ISGF2 (IRF–1) Can Bind to the Promoters of Both Beta Interferon– and Interferon–Stimulated Genes but Is Not a Primary Transcriptional Activator of Either", *Molecular and Cellular Biology* 10(6):2448–2457(1990).

B.D. Clark et al., "Genomic sequence for human prointerleukin 1 beta: possible evolution from a reverse transcribed prointerleukin 1 alpha gene", *Nuc. Acids. Res.* 14:7897–7915 (1986).

Kominato et al., "Monocyte Expression of the Human Prointerleukin 1β Gene (IL1B) Is Dependent on Promoter Sequences Which Bind the Hematopoietic Transcription Factor Spi–1/PU.1", *Mol. Cell. Bio.* 15(1):58–68 (1995).

Fenton et al., "Transcriptional Regulation of the Human Prointerleukin 1β Gene", *J. Immunol.* 138(11):3972–3979 (1987).

Kotanides et al., "Requirement of Tyrosine Phosphorylation for Rapid Activation of a DNA Binding Factor by IL–4", *Science* 262:1265–1267 (1993).

Dignam et al., "Accurate transcription initiation by RNA polymerase II in a soluble extract from isolated mammalian cell nuclei", *Nucl. Acids. Res.* 11(5):1475–1489 (1983).

Prywes et al., "Inducible Binding of a Factor to the c–fos Enhancer", *Cell* 47:777–784 (1986).

Shirakawa et al., "In Vitro Activation and Nuclear Translocation of NF–kB Catalyzed by Cyclic AMP–Dependent Protein Kinase and Protein Kinase C", *Mol. Cell. Bio.* 9(6):2424–2430 (1989).

C.A. Dinarello, "The interleukin–1 family: 10 years of discovery", *FASEB J.* 8:1314–1325 (1994).

S. Akira et al., "Biology of multifunctional cytokines: IL 6 and related molecules (IL 1 and TNF)", *FASEB J.* 4:2860–2867 (1990).

F. Shirakawa et al., "Interleukin 1 and Cyclic AMP Induce k Immunoglobulin Light–Chain Expression via Activation of an NF–kB–Like DNA–Binding Protein", *Mol. Cell Biol.* 9(3):959–964 (1989).

W. Conca et al., "An Interleukin 1β Point Mutant Demonstrates That jun/fos Expression Is Not Sufficient for Fibroblast Metalloproteinase Expression", *J. Biol. Chem.* 266(25):16265–16268 (1991).

S.D. Wright and M.T. Jong, "Adhesion–Promoting Receptors on Human Macrophages Recognize *Escherichia Coli* by Binding to Lipopolysaccharide", *J. Exp. Med.* 164:1876–1888 (1986).

C. Couturier et al., "Binding Sites for Endotoxins (Lipopolysaccharides) on Human Monocytes", *J. Immunol.* 147(6):1899–1904 (1991).

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

T T N C N N A G A      9

( 2 ) INFORMATION FOR SEQ ID NO:2:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

T T C C T G A G A      9

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGCTTATAAG AGGTTTCACT TCCTGAGAGT CGA            33

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CGATCGAGAT GTATTTCCCA GAAAAGTCGA            30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CGATCGAGAT GTATGGCCCA GACAAGTCGA            30

( 2 ) INFORMATION FOR SEQ ID NO:6:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TTCCTGTAA            9

( 2 ) INFORMATION FOR SEQ ID NO:7:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TTCCCGTAA            9

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

ATAAGAGSTK KCACKKCCTG AGM            23

LIL-STAT DNA BINDING SITES AND METHODS FOR IDENTIFYING INHIBITORY BINDING AGENTS

The U.S. Government has a paid-up license in this invention and the right in limited circumstances to require the patent owner to license others on reasonable terms as provided for by the terms of Grant Nos. AI27850 and AR03564 awarded by the National Institutes of Health.

FIELD OF THE INVENTION

This invention relates to novel DNA sequences which are binding sites for the LIL-Stat protein, and to methods for identifying agents which inhibit interaction between the LIL-Stat protein and these binding sites.

BACKGROUND OF THE INVENTION

Inflammation is a serious and widespread medical problem. It contributes to such diseases as rheumatoid arthritis, septic shock, respiratory distress syndrome, chronic hepatitis B, thermal injury (burns), Kawasaki's disease, Paget's disease, inflammatory bowel disease, inflammatory carcinoma and other diseases. Cytokine proteins regulate a large array of mammalian cellular activation, growth and differentiation processes. Interleukin 1β is a cytokine that is involved in inflammatory processes. It is produced by activated monocytes/macrophages, fibroblasts, endothelial cells and other cell types. The interleukin 1β gene is normally not transcribed is such cells until activated by a stimulant such as lipopolysaccharide, the IL-1 proteins or phorbol myristate acetate. At least two general regions have been reported which are involved in expression of the interleukin 1β gene. One region is the promoter which is located between positions −131 and +12 relative to the transcription start site and confers tissue specificity upon the gene primarily by virtue of the binding of a tissue-restricted transcription factor. Kominato et al., Mol. Cell. Bio. 15:58–68 (1995). A second region, located far upstream from the transcription start site, between positions −3134 to −2729, confers induction responsiveness upon the interleukin 1 gene. Shirakawa et al., Mol. Cell. Biol. 13:1332–1334 (1993); Tsukada et al., Mol. Cell. Biol. 14:7285–7297 (1994). Various binding sites and transcription factors, including NF-1L6 (C/EBPβ), NF-κB, CREB and other CREB-like proteins, which are partially involved in the transcriptional regulation of the interleukin 1 gene have previously been reported. Previous reports, however, have not completely elucidated all of the transcription factors and sites involved in regulation of the interleukin 1β gene.

There is a need for therapeutic agents which can effectively inhibit transcription of the interleukin 1β gene and other pro-inflammatory genes induced by agents such as bacteria, LPS, and IL-1 proteins, thereby ameliorating the inflammatory response which is mediated by these genes.

SUMMARY OF THE INVENTION

It is an object of the invention to identify therapeutic agents which can be used for treating or preventing inflammation in a mammal.

It is yet another object of the invention to identify agents which inhibit interaction between LIL-Stat protein and its binding site.

It is yet another object of the invention to provide a safe, effective, easy and inexpensive method for treating or preventing inflammation in a mammal.

It is yet another object of the invention to treat or prevent inflammation by administering to a mammal an agent which inhibits interaction between LIL-Stat protein and its binding site, so as to reduce production of interleukin 1β.

Still another object of the invention is to provide a method for treating or preventing inflammation by administering an agent which inhibits at least interleukin 1 or LPS functions, and in which these functions are restored upon depletion of the agent.

According to the invention, a method for finding an agent which inhibits interaction between LIL-Stat protein and a nucleic acid having a LIL-Stat binding sequence is provided. The LIL-Stat protein is contacted with the nucleic acid in the presence of an agent which inhibits or does not inhibit the interaction between the LIL-Stat protein and the nucleic acid. It is determined, preferably by an electrophoretic mobility shift assay or a solid phase affinity assay, whether or not the agent inhibits this interaction. In certain embodiments, the LIL-Stat binding sequence is a DNA sequence which consists essentially of the sequence: TTNCNNAGA. (Sequence ID No. 1). The sequence preferably is TTCCTGAGA. (Sequence ID No. 2).

Another aspect of the invention is a method of screening for an agent which inhibits interaction between LIL-Stat protein and a nucleic acid having a LIL-Stat binding sequence. Test cells and reference cells are separately provided. The test cells and reference cells are treated with a stimulant, e.g., lipopolysaccharide, IL-1 proteins, phorbol myristate acetate, cell adherents to glass or polystyrene, complement proteins, calcium ionophores, β-glucan polymers, or mixtures thereof. The test cells are treated with a test agent. Nuclear extracts are prepared from the test cells and from the reference cells, and these nuclear extracts are each contacted with a nucleic acid having a LIL-Stat protein binding sequence. The binding between the nuclear extract from the test cells and the nucleic acid is compared to the binding between the nuclear extract from the reference cells and the nucleic acid, so as to determine the presence or absence of any differential binding. A determination is made as to whether or not the test agent inhibits interaction between the LIL-Stat protein and the nucleic acid having the LIL-Stat binding sequence based upon the presence or absence of any differential binding.

In certain embodiments, the reference cells and the test cells are the same type of cells, preferably T cells, fibroblasts, monocytes, or other cells responsive to IL-proteins, LPS, or other stimulants of LIL-Stat protein. Variations of this method include using cells from a cell culture, a perfused tissue or an animal.

Another aspect of the invention features a method of screening for an agent which inhibits interaction between LIL-Stat protein and a nucleic acid having a LIL-Stat binding sequence. Cells are provided, and the cells are treated with a stimulant, e.g., lipopolysaccharide, IL-1 proteins or phorbol myristate acetate, and with a test agent. A nuclear extract is prepared from these cells and the nuclear extract is contacted with a nucleic acid having a LIL-Stat binding sequence. It is determined whether there is any binding between the nuclear extract and the nucleic acid. An agent which inhibits interaction between LIL-Stat protein and the nucleic acid is identified by a reduction in the binding between the LIL-Stat protein and the nucleic acid as compared to cells which have been identically treated except that no test agent is added.

Yet another aspect of the invention features a method for finding an agent which inhibits interaction between LIL-Stat protein and a nucleic acid having a LIL-Stat binding sequence. A predetermined cell extract is contacted with an agent which inhibits or does not inhibit such interaction, utilizing a stimulant which enables LIL-Stat protein production. It is determined whether or not the agent inhibits the interaction of the LIL-Stat protein and the nucleic acid.

The invention also features a method for treating an inflammatory response in a mammal. An agent is provided which is effective to inhibit interaction between LIL-Stat protein and a nucleic acid having a LIL-Stat binding sequence. The agent is administered to a mammal in need of such treatment to cause this inhibition to occur.

In addition, a therapeutic inhibitory agent in a dosage form and concentration which is suitable for treating or preventing an inflammatory response in a mammal in need of such treatment is provided. The inhibitory agent is effective to inhibit interaction between LIL-Stat protein and a nucleic acid having a LIL-Stat binding sequence.

Another aspect of the invention is an isolated DNA molecule having a DNA sequence encoding a binding site for LIL-Stat protein. This sequence consists essentially of TTNCNNAGA (Sequence ID No. 1). Preferably, the sequence consists essentially of TTCCTGAGA (Sequence ID No. 2). In certain embodiments the DNA has a 5' flanking sequence to the binding site which preferably is about 1 to about 100 nucleotides in length, more preferably is about 1 to about 50 nucleotides in length, and most preferably is about 1 to about 10 nucleotides in length. In other embodiments, the DNA has a 3' flanking sequence to the binding site which preferably is about 1 to about 100 nucleotides in length, more preferably is about 1 to about 50 nucleotides in length, and most preferably is about 1 to about 10 nucleotides in length.

The invention also features a DNA vector having a binding site for LIL-Stat protein. The invention further features a transformed cell having a foreign nucleic acid which has a binding site for the LIL-Stat protein.

The above and other objects, features and advantages of the present invention will be better understood from the following specification when read in conjunction with the accompanying drawings.

DETAILED DESCRIPTION

Figure 1:
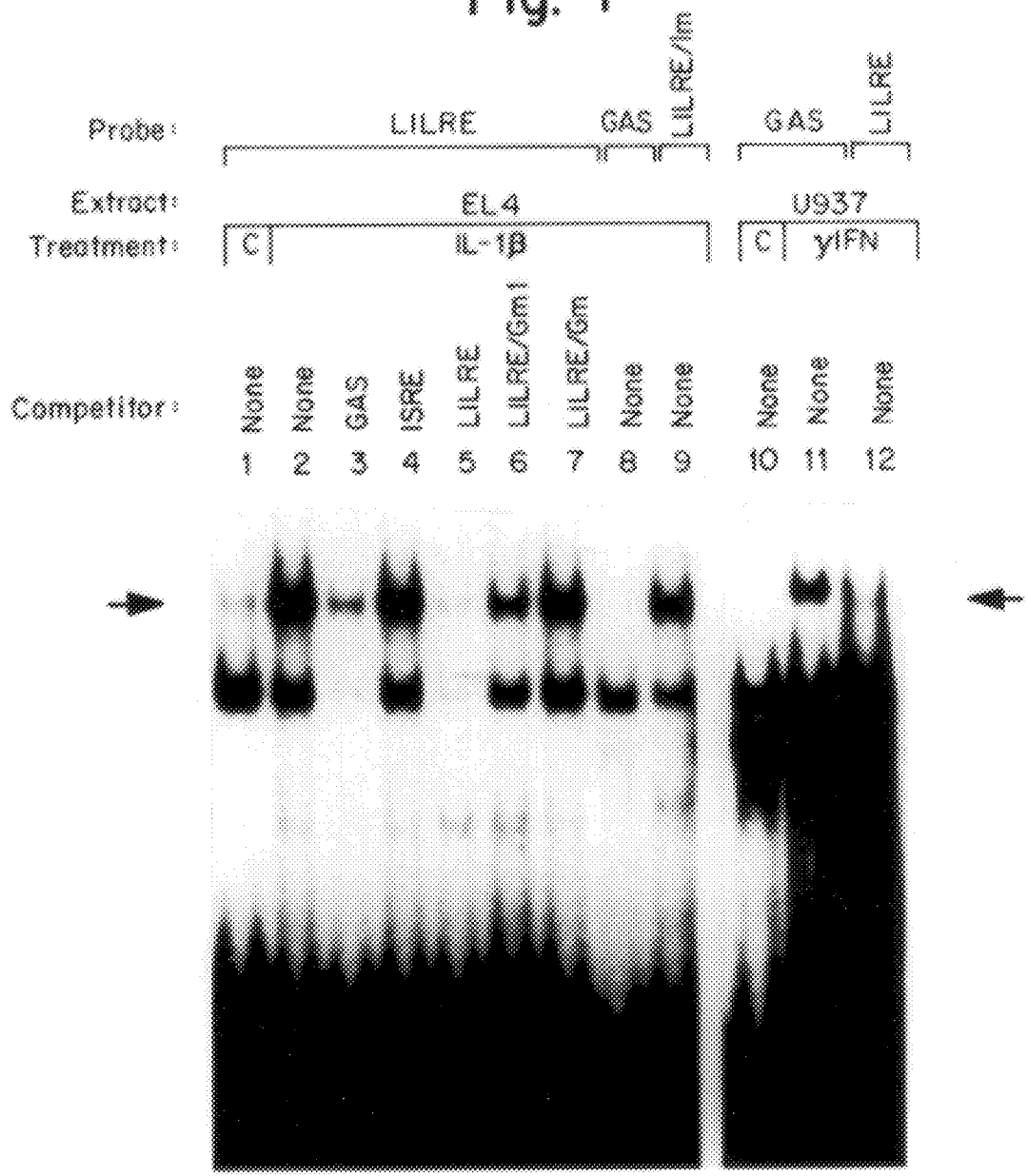
FIG. 1 depicts EMSA of DNA binding proteins induced by IL-1β.

This invention provides a method for finding an agent which inhibits interaction between LIL-Stat protein and a nucleic acid having a LIL-Stat binding sequence. The LIL-Stat protein is contacted with the nucleic acid in the presence of an agent which inhibits or does not inhibit the interaction between the LIL-Stat protein and the nucleic acid. It is determined whether or not the agent inhibits this interaction.

By LIL-Stat protein is meant a protein which is a novel member of the Stat family of transcription factors which is involved in the induction of the cytokine interleukin 1β gene, a gene having a key role as a mediator of inflammation. The LIL-Stat protein can be induced by various stimulants, e.g., lipopolysaccharide (LPS), the IL-1 proteins, and mixtures thereof.

The LIL-Stat protein recognizes a DNA binding site which is distinct from the binding sites for other known Stat proteins. This binding site is normally located upstream from the transcription start site for the interleukin 1β gene within sequence −2863 to −2841, and specifically at −2849 to −2841. This DNA binding site (the LIL-Stat binding site) does not efficiently bind other known Stat proteins. The LIL-Stat binding sequence (at position −2849 to −2841) comprises a DNA sequence which consists essentially of the sequence: TTNCNNAGA. (Sequence ID No. 1). A preferred sequence is TTCCTGAGA. (Sequence ID No. 2). The LIL-Stat binding sequence used in this invention for finding an inhibitory agent can in certain embodiments have a 5' and/or a 3' flanking sequence. Preferably, these flanking sequences are about 1 to about 100 nucleotides in length, more preferably about 1 to about 50 nucleotides in length, and most preferably about 1 to about 10 nucleotides in length. In certain embodiments, other regulatory sequences and/or structural gene sequences can also be present on the nucleic acid molecule which has the LIL-Stat binding sequence. In other embodiments, the LIL-Stat binding sequence can be part of a vector. A vector is meant to include, e.g., plasmids, viruses and phage.

The agent of this invention can inhibit interaction between the LIL-Stat protein and the LIL-Stat binding sequence. Inhibiting interaction includes partial or complete inhibition. By inhibiting interaction is meant, e.g., that the LIL-Stat protein and the LIL-Stat binding sequence are unable to properly bind to each other. By properly bind to each other is meant that if such binding were to occur in vivo in a wild type cell, the binding would be such as to enable normal induction of transcription of the interleukin 1β gene or any other gene containing a LIL-Stat binding sequence if all other requirements for such induction were also present.

Such inhibition can be the result of any one of a variety of events, including, e.g., preventing or reducing interaction between the LIL-Stat protein and its binding site; inactivating the LIL-Stat protein, e.g., by cleavage or other modification; altering the affinity of LIL-Stat protein and the binding site for each other; diluting out the LIL-Stat protein and/or the binding site; preventing expression of the LIL-Stat protein; interfering with activation of the LIL-Stat protein, e.g., interfering with dimerization required for DNA binding of the LIL-Stat protein; reducing synthesis of the LIL-Stat protein; synthesizing an abnormal LIL-Stat protein; synthesizing an alternatively spliced LIL-Stat protein; preventing or reducing proper conformational folding of the LIL-Stat protein; modulating the binding properties of the LIL-Stat protein and/or the binding site; interfering with signals that are required to activate or deactivate the LIL-Stat protein and/or the binding site; activating or deactivating the LIL-Stat protein and/or the binding site at the wrong time; or interfering with other regulatory elements or other molecules or sites which are required for the normal synthesis or functioning of the LIL-Stat protein and/or its binding site. Examples of agents include synthetic analogs of LIL-Stat protein, inhibitory proteins, inhibitory peptides, inhibitory carbohydrates, inhibitory glycoproteins, inhibitory glycopeptides, and inhibitors of a molecule required for the synthesis or functioning of LIL-Stat protein.

A preferred agent is a substance that interferes with the phospho-tyrosine mediated dimerization required for DNA binding of the LIL-Stat protein. Such agents include, e.g., short phospho-tyrosine peptides, preferably about 4 to about 15 amino acids long, or these peptides incorporated into larger proteins, which can competitively disrupt LIL-Stat protein dimer formation; small molecules analogous to phospho-tyrosine or phenyl-phosphate; tyrosine phosphatases or other compounds which make active tyrosine phosphatases that inhibit LIL-Stat protein dimerization; and double stranded oligonucleotides, e.g., phosphorothioate DNA, which contain a LIL-Stat binding site.

Agents are also meant to include, e.g., anti-LIL-Stat protein antibodies. The antibodies can be directed against the LIL-Stat protein or a subunit or fragment thereof. Both polyclonal and monoclonal antibodies can be used in this invention.

Synthetic analogs or mimetics of the LIL-Stat protein or the LIL-Stat binding site also can serve as agents. LIL-Stat analogs or mimetics are substances which resemble in shape and/or charge distribution LIL-Stat protein. An analog of at least a portion of the LIL-Stat protein can compete with its naturally occurring cognate LIL-Stat protein for the binding site on the DNA, and thereby reduce or eliminate binding between the naturally occurring LIL-Stat protein and the DNA binding site. Analogs of the LIL-Stat binding site include, e.g., phosphorothioate oligonucleotides and protein nucleic acid analogs.

Agents are also meant to include inhibitors of a molecule that is required for synthesis, post-translational modification, or functioning of the LIL-Stat protein, or activators of a molecule that inhibits the synthesis or functioning of the LIL-Stat protein. Agents include, e.g., cytokines, growth factors, hormones, signaling components, kinases, phosphatases, homeobox proteins, transcription factors, translation factors and post-translation factors or enzymes. Agents also include, e.g., ionizing radiation, non-ionizing radiation, ultrasound and toxic agents which can, e.g., at least partially inactivate or destroy LIL-Stat protein.

An agent is also meant to include inhibitors which are not entirely LIL-Stat protein specific. For example, an agent may inhibit interactions of other Stat proteins in addition to LIL-Stat interactions. Such overlapping specificity may provide additional therapeutic advantage.

In this method of the invention, a determination is made as to whether or not the agent does inhibit interaction of the LIL-Stat protein and a nucleic acid having a LIL-Stat binding sequence. Any method which measures binding of the LIL-Stat protein to its DNA binding sequence can be used in this invention. Such methods include, e.g., electrophoresis, chromatography, centrifugation and solid phase binding, e.g., biotin/avidin affinity columns, UV cross-linked nitrocellulose, and other procedures known to those skilled in the art. A preferred method is electrophoresis, e.g., using an electrophoretic migration shift assay (EMSA) in which the presence or absence of binding is analyzed, preferably by polyacrylamide gel electrophoresis. Example 5 describes one embodiment of such an assay. Another preferred assay is a solid phase affinity assay.

The agent identified by this method as inhibiting interaction between LIL-Stat protein and a nucleic acid having a LIL-Stat binding sequence is also included in this invention.

The invention also includes a method of screening for an agent which inhibits interaction between LIL-Stat protein and a nucleic acid having a LIL-Stat binding sequence. Test cells and reference cells are separately provided. The test cells and reference cells are treated with a stimulant. The test cells are treated with a test agent. Nuclear extracts are prepared from the test cells and from the reference cells, and these nuclear extracts are each contacted with a nucleic acid having a LIL-Stat binding sequence. The binding between the nuclear extract from the test cells and the nucleic acid is compared to the binding between the nuclear extract from the reference cells and the nucleic acid, so as to determine the presence or absence of any differential binding. A determination is made as to whether or not the test agent inhibits interaction between the LIL-Stat protein and the nucleic acid having the LIL-Stat binding sequence based upon the presence or absence of any differential binding.

By reference cells is meant cells to which no test agent is added. By test cells is meant cells to which a test agent is added. Preferably, the reference cells and the test cells are the same type of cells. Any cells which are inducible for the LIL-Stat protein can be used. Preferred cells are T cells, fibroblasts, monocytes or any other cells that respond to IL-1 proteins, LPS or other stimulants of LIL-Stat protein. Cells which are treated with the stimulant and/or agent can be, e.g., cells from a cell culture, a perfused tissue or an animal. The stimulant and/or agent can be, e.g., added directly to the cell culture, poured onto the tissue, or administered to the animal by any method where access to the target cells in obtained, e.g., by injection, e.g., intravenous, intradermal, subcutaneous, intramuscular or intraperitoneal; deposition; implantation, e.g., by inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets; suppositories; oral ingestion; inhalation, e.g., administering the agent with an aerosol in an inhalator, either alone or attached to a carrier; or topical administration.

By stimulant is meant any substance which can induce cells to produce LIL-Stat protein. Examples of stimulants include lipopolysaccharide, IL-1 proteins, phorbol myristate acetate, cell adherents to glass or polystyrene, complement proteins, e.g., C5a, calcium ionophores, β-glucan polymers, and mixtures thereof. Preferred stimulants are lipopolysaccharide and IL-1 proteins. The cells can be treated with the stimulant prior to, or subsequent to, treatment with the test agent.

The nuclear extracts can be prepared by any of a variety of methods known to those skilled in the art. See Example 5 for one such embodiment. Preferably, the nuclear extracts are treated with one or more protease inhibitors, e.g., antipain, aprotinin, cymostatin, leupeptin and pepstatin A, and/or one or more phosphatase inhibitors, e.g., $MnCl_2$, orthovanadate, NaF, sodium pyrophosphate and β-glycerophosphate. The assays for binding are as discussed above.

The agent identified by this method as inhibiting interaction between LIL-Stat protein and a nucleic acid having a LIL-Stat binding sequence is also included in this invention.

The invention also includes a method of screening for an agent which inhibits interaction between LIL-Stat protein and a nucleic acid having a LIL-Stat protein binding sequence. Cells are provided, and the cells are treated with a stimulant and with a test agent. A nuclear extract is prepared from these cells and the nuclear extract is contacted with a nucleic acid having a LIL-Stat protein binding sequence. It is determined whether there is any binding between the nuclear extract and the nucleic acid. An agent which inhibits interaction between LIL-Stat protein and the nucleic acid is identified by a reduction in the binding between the LIL-Stat protein and the nucleic acid as compared to cells which have been identically treated except that no test agent is added.

The invention further includes a method for finding an agent which inhibits interaction between LIL-Stat protein and a nucleic acid having a LIL-Stat binding sequence. A predetermined cell extract is contacted with an agent which inhibits or does not inhibit such interaction, utilizing a stimulant which enables LIL-Stat protein production. It is determined whether or not the agent inhibits the interaction of the LIL-Stat protein and the nucleic acid.

By predetermined cell extract is meant a cell extract derived from a particular type of cell. Any cells which are inducibile for the LIL-Stat protein can be used.

This invention further provides a method for treating an inflammatory response in a mammal. An agent is provided which is effective to inhibit interaction between LIL-Stat protein and a nucleic acid having a LIL-Stat binding sequence. The agent is administered to a mammal in need of such treatment to cause this inhibition to occur.

By inflammatory response is meant a condition of inflammation which is at least partially mediated by the cytokine interleukin 1β gene. By mammals is meant human as well as non-human mammals. Treating an inflammatory response is meant to include preventing, arresting, altering or reversing the inflammation. In certain embodiments the nucleic acid has a sequence which consists essentially of TTNCNNAGA (Sequence ID No. 1). A preferred sequence is TTCCTGAGA (Sequence ID No. 2). 5' and 3' flanking regions, and other sequences, can also be present as discussed above.

Administration of the agent can be accomplished by any method which allows the agent to reach the target cells, as discussed above. Administration of the agent can be alone or in combination with other therapeutic agents. In certain embodiments, the agent can be combined with a suitable carrier, incorporated into a liposome, or incorporated into a polymer release system.

In certain embodiments of the invention, the administration can be designed so as to result in sequential exposures to the agent over some time period, e.g., hours, days, weeks, months or years. This can be accomplished by repeated administrations of the agent by one of the methods described above, or alternatively, by a controlled release delivery system in which the agent is delivered to the mammal over a prolonged period without repeated administrations. By a controlled release delivery system is meant that total release of the agent does not occur immediately upon administration, but rather is delayed for some time period. Release can occur in bursts or it can occur gradually and continuously. Administration of such a system can be, e.g., by long acting oral dosage forms, bolus injections, transdermal patches and subcutaneous implants.

Examples of systems in which release occurs in bursts include, e.g., systems in which the agent is entrapped in liposomes which are encapsulated in a polymer matrix, the liposomes being sensitive to a specific stimuli, e.g., temperature, pH, light or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

The agent can be suspended in a liquid, e.g., in dissolved form or colloidal form. The liquid can be a solvent, partial solvent or non-solvent. In many cases water or an organic liquid can be used. The agent can be administered prior to or subsequent to the onset of inflammation.

The agent is administered to the mammal in a therapeutically effective amount. By therapeutically effective amount is meant that amount which is capable of at least partially preventing or reversing the inflammation. A therapeutically effective amount can be determined on an individual basis and will be based, at least in part, on consideration of the species of mammal, the mammal's size, the agent used, the type of delivery system used, the time of administration relative to the onset of inflammation and whether a single, multiple, or controlled release dose regimen is employed. A therapeutically effective amount can be determined by one of ordinary skill in the art employing such factors and using no more than routine experimentation.

Preferably, the concentration of the agent, if applied systemically, is at a dose of about 0.1 to about 500 mg/kg body weight. Most preferably the dose is about 0.1 to about 5 mg/kg. The specific concentration partially depends upon the particular agent used, as some are more effective than others. The dosage concentration of the agent that is actually administered is dependent at least in part upon the final concentration that is desired at the site of action, the method of administration, the efficacy of the particular agent, the longevity of the particular agent, and the timing of administration relative to the onset of the inflammatory response. Preferably, the dosage form is such that it does not substantially deleteriously affect the mammal. The dosage can be determined by one of ordinary skill in the art employing such factors and using no more than routine experimentation.

The agents of the invention are meant to include reversible and non-reversible agents. If an agent is reversible, the inhibition of the interaction between LIL-Stat protein and the LIL-Stat binding sequence will be reversed at some point after administration of the agent ceases. A reversible agent is preferable in that it permits discontinuation of administration of the agent during periods when production of interleukin 1β is desired. Interleukin 1β function is thereby restored and able to act in its inflammation response capacity to aid in fighting infections or in wound repair, or in its other capacities.

In another aspect, the invention features a therapeutic inhibitory agent in a dosage form and concentration which is suitable for treating or preventing an inflammatory response in a mammal in need of such treatment. The inhibitory agent is effective to inhibit interaction between LIL-Stat protein and a nucleic acid having a LIL-Stat binding sequence.

The invention also includes an isolated DNA molecule having a DNA sequence encoding a binding site for LIL-Stat protein. This sequence consists essentially of TTNCN-NAGA (Sequence ID No. 1). Preferably, the sequence consists essentially of TTCCTGAGA (Sequence ID No. 2). In certain embodiments, the DNA has a 5' flanking sequence to the binding site, which preferably is about 1 to about 100 nucleotides in length, more preferably is about 1 to about 50 nucleotides in length, and most preferably is about 1 to about 10 nucleotides in length. In other embodiments the DNA has a 3' flanking sequence to the binding site, which preferably is about 1 to about 100 nucleotides in length, more preferably is about 1 to about 50 nucleotides in length, and most preferably is about 1 to about 10 nucleotides in length.

The invention also includes a DNA vector having a binding site for LIL-Stat protein. The invention further includes a transformed cell having a foreign nucleic acid which has a binding site for the LIL-Stat protein.

The LIL-Stat binding sequence can be used, e.g., as a reagent in methods for identifying agents, both natural and synthetic, which inhibit interaction between the LIL-Stat protein and the LIL-Stat binding sequence. Such agents are useful therapeutic compounds in treating inflammation which is at least partially mediated by the interleukin 1β gene. The LIL-Stat binding sequence can also be used as a reagent for identifying proteins, e.g., expressed proteins from cDNA libraries which specifically bind to that sequence, but not to the other classes of Stat binding sequences. Thus, the LIL-Stat binding sequence is useful for cloning the LIL-Stat protein. Moreover, because other members of the Stat family have been demonstrated to specifically interact with specific phospho-tyrosine peptides with specific receptor signalling domains, the LIL-Stat binding site (which is an SH2-like phospho-tyrosine binding site), can also be used as an affinity reagent, e.g., as a LIL-Stat SH2 domain-glutathione-S-transferase fusion protein, to identify other proteins which are involved in both IL-1 proteins and LPS signalling. The LIL-Stat binding sequence can further be used as a basis for an EMSA assay for LIL-Stat induction in order to map specific regions of the IL-1 receptor for function following deletion or site specific mutation. Such an approach can be used to determine which regions or amino acids are important for IL-1 signalling critical for inflammation.

EXAMPLES

Example 1
INDUCTION BY LPS or IL-1 Produces A LIL-Stat Protein With Unique Binding Affinities This example illustrates that induction of cells by either LPS or IL-1 results in production of LIL-Stat protein which binds to a unique DNA binding site within the LILRE GAS sequence, but not the ISRE sequence.

ISRE sites bind non-Stat proteins of the ISGF family. (Darnell et al., Science 264:1415–1421 (1994)). In response to α/β interferon receptor signaling, Stat1 and the distinct Stat2 protein (which is not induced by γ IFN) are activated to associate with ISGF3γ, increasing its avidity for the ISRE (Interferon Stimulated Response Element) (Darnell et al., Science 264:1415 (1994)). In this way, Stat1, which does not directly bind the ISRE, can also mediate ISRE activity. In order to examine proteins which bind to the IL1β gene LPS/IL-1 response element (LILRE), induction of nuclear factors from LPS and IL-1 responsive cells was evaluated by electrophoretic mobility shift assay (EMSA) using $^{32}$P-labeled DNA containing a GAS site (Darnell et al., Science 264:1415–1421 (1994)) derived from the FCγRI gene (Pearse et al., Proc. Natl. Acad. Sci. USA 90:4314 (1993)) or the LILRE.

FIG. 1 shows EMSA of DNA binding proteins induced by IL-1β and LPS. The growth conditions and induction protocols are described in Shirakawa et al., Mol. Cell. Biol. 13:1332–1344 (1993). Nuclear extracts were prepared from control (C) and treated (as indicated) murine EL4 thymoma, human primary dermal fibroblasts, and human monocytes (U937 and THP-1), in the presence of 3.55 μM cycloheximide as described in Fenton et al., J. Immunol. 138:3972–3979 (1987). The oligonucleotide sequences used were as follows: LILRE, 5'-AGCTTATAAGAGGTTTCACTTCCTGAGAGTCGA-3' (Sequence ID No. 3); GAS, 5'-CGATCGAGATGTATTTCCCAGAAAAGTCGA-3' (Sequence ID No. 4); and GASm mutant, 5'-CGATCGAGATGTATGGCCCAGACAAGTCGA-3' (Sequence ID No. 5). The LILRE mutants LILRE/Im, LILRE/Gm, and LILRE/Gml contained the substitutions shown in FIG. 3. Oligonucleotide probes were labeled with [$^{32}$P] nucleotide triphosphates and Klenow enzyme as previously reported (Shirakawa et al., Mol. Cell. Biol. 13:1332–1334 (1993)). Unlabeled competitor oligonucleotides were used at a 50-fold molar excess over radiolabeled probe. The arrow locates the mobility of the inducible factor common to both IL-1β and LPS induction. (A) is specificity of IL-1β and (B) is specificity of LPS induced DNA binding factors.

Treatment of the cells with either IL-1β (FIG. 1, lanes 1–2) or LPS (FIG. 2, lanes 1–2) for 15 minutes in the presence of the protein synthesis inhibitor cycloheximide revealed a protein capable of binding to the LILRE probe. The LPS and IL-1 induced proteins behaved similarly in terms of electrophoretic migration and competition (FIG. 1, lanes 3–7 and FIG. 2, lanes 3–8) with unlabeled oligonucleotides containing known GAS and ISRE sites, a mutated GAS site, the native LILRE sequence, and three different mutated LILRE sequences as shown in FIG. 3.

Figure 3:
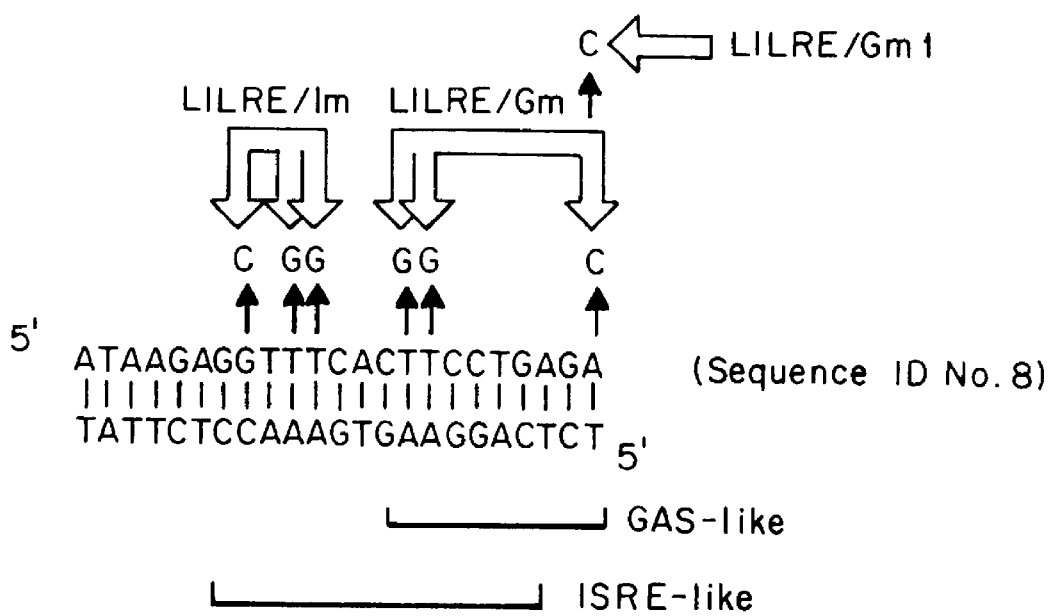
FIG. 3 depicts the LILRE (LPS/IL-1 Responsive Element) sequence contained within the human IL-1β gene.

FIG. 3 depicts the LPS/IL-1 responsive element (LILRE) sequence contained within the human IL1β gene. The sequence corresponds to positions −2863 to −2841 of the gene (GenBank Accession No. L06808). Brackets below the sequence locate GAS and ISRE-like motifs. Large open arrows identify mutations contained in three distinct oligonucleotides. The specific nucleotide substitutions are indicated by small solid arrows.

Figure 2:
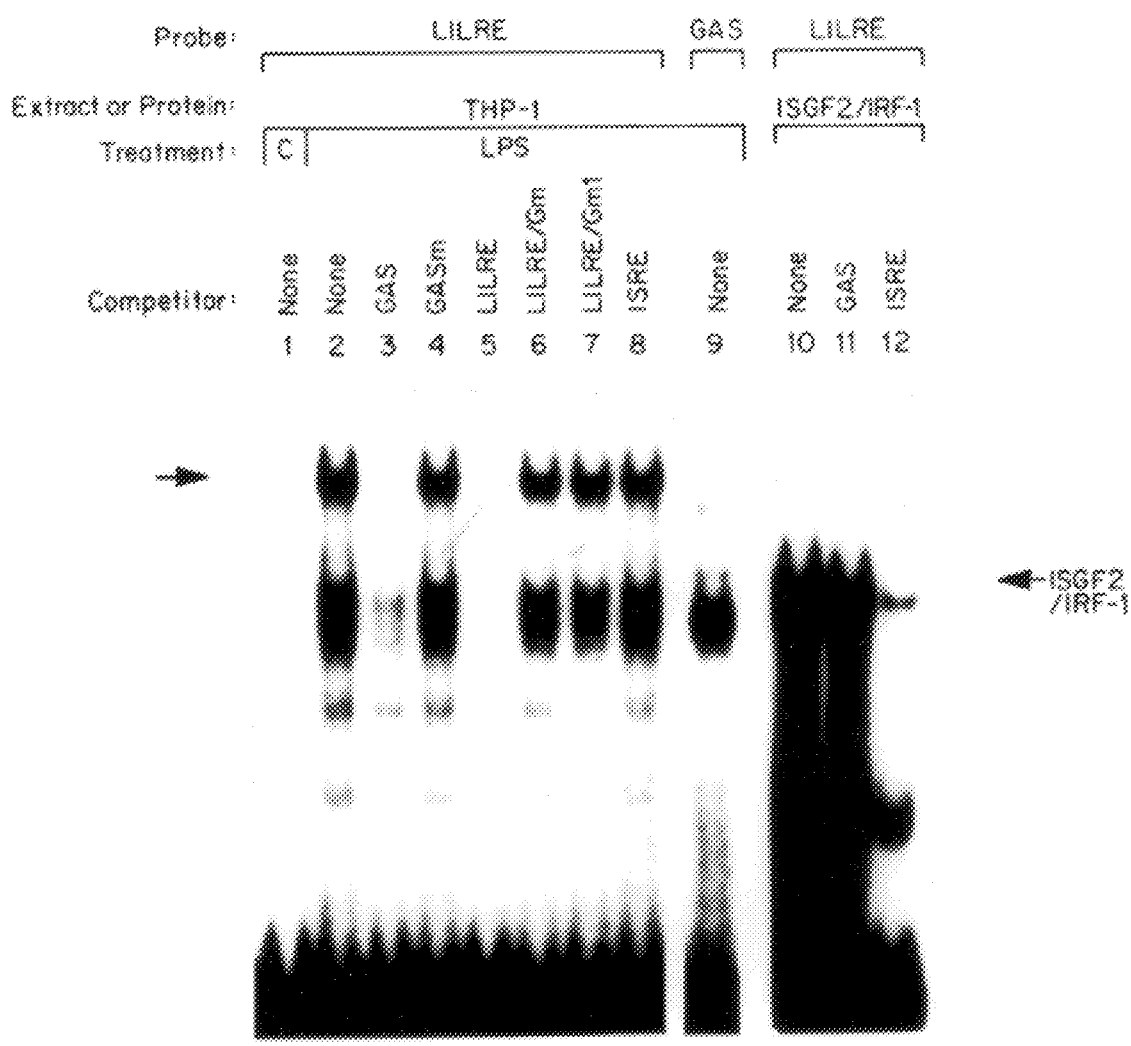
FIG. 2 depicts EMSA of DNA binding proteins induced by LPS.

The above results indicate that the LILRE can bind a Stat-like protein as judged by the competition with a 50-fold molar excess of unlabeled GAS DNA (FIGS. 1 and 2, lanes 3). However, radiolabeled GAS probe could not bind efficiently to either the IL-1 (FIG. 1, lane 8) or LPS (FIG. 2, lane 9) induced factors, consistent with an earlier report that neither IL-1 nor LPS can induce binding to an FcγRI GAS target site (Larner et al., Science 261:1730(1993)). In contrast, the GAS probe could bind its cognate Stat1 factor derived from γIFN treated cells (FIG. 1, lane 11). Reciprocally, the LILRE probe did not efficiently bind Stat1 (FIG. 1, lane 12). Therefore, GAS only weakly binds the LPS/IL-1 factor (the LIL factor). Although the ISRE site within the LILRE is not the target of the LIL factor, the ISRE binding site was capable of specifically binding the ISRE binding protein ISGF2/IRF-1. Therefore, binding to the LILRE GAS site, and not the ISRE site, results from immediate early signals induced by either LPS or IL-1.

Example 2
The Binding Site Specificity of the LIL-Stat Protein Is Distinct From Other Known Stat Proteins This example illustrates that the binding site specificity of the LIL-Stat protein is distinct from that of any known Stat proteins. Binding of LIL-Stat protein to GAS probe is extremely low, indicating that the LIL-Stat factor is a novel protein. Binding studies were conducted in the presence of specific anti-Stat antibodies. The IL-1β and LPS induced DNA binding protein is antigenically related to the amino terminus of Stat1, but not to the carboxyl terminus of either Stat1 or Stat3. EMSAs were conducted as described in Example 1, but in the presence of antisera. Stat1N antibody (#G16920) (from Transduction Laboratories, Lexington, Ky.), Stat1C antibody (#SC346) and ISGF3γ (#SC496) (from Santa Cruz Biotechnology, Inc., Santa Cruz, Calif.), and Stat3 antibody described in Akira et al., Cell 77:63–71 (1994), were independently tested for specificity using radiolabeled GAS probe and additional nuclear extracts derived from γIFN treated human U937 cells and IL-6 treated human Hep3B hepatocytes. IL-1β induced extract was incubated with either 1 or 2 μl of increasing concentrations of antibody. LPS induced extract was incubated with 2 μl of increasing antibody concentrations. These experiments revealed that those antibodies specific for C-terminal regions of Stat proteins and the ISRE binding factor ISGF3γ did not cross-react with LIL-Stat, whereas an antibody raised toward the N-terminal 194 amino acids of Stat1 which contains invariant amino acids conserved among Stat family members (Zhong et al., Proc. Natl. Acad. Sci. USA 91:4806 (1994)) did abrogate DNA binding for both LPS and IL-1 treated extracts. Therefore, the LIL-Stat factor is a member of the Stat family distinct from Stat1 and Stat3.

The IL-4 induced Stat6 protein (Hou et al., Science 265:1701 (1994)) is also not the LIL factor (LIL-Stat) because the Stat6•DNA complex possesses the distinct EMSA mobility previously reported (Kotanides et al., Science 262:1265 (1993)). In addition, the Stat6 complex is only weakly competed by a 50-fold molar excess of unlabeled LILRE. Because LIL-Stat is also strongly induced by IL-1 in cultured primary human dermal fibroblasts, it is also not Stat4, which has been reported to be absent in fibroblasts and constitutively expressed in many monocyte cell lines (Yamamoto et al., Mol. Cell. Biol. 14:4342 (1994)). It has been reported that the uncharacterized Stat factors induced by other cytokines such as IL-3, IL-5, IL-10, and GM-CSF bind well to the FcγRI GAS probe (Larner et al., Science 261:1730 (1993)), further substantiating the uniqueness of LIL-Stat. Finally, Stat5 which is induced by prolactin requires a G residue at position 7 of its specific GAS sequence (Wakao et al., EMBO J. 13:2182–2191 (1994)), which argues that LIL-Stat is distinct from Stat5. The apparent distinctness of LIL-Stat from the above-mentioned Stat factors is consistent with a specific induction by LPS and IL-1 and not by IL-6, IL-4, and γIFN. Furthermore, the lack of strong GAS avidity indicates that LIL-Stat is distinct from other known Stats.

Example 3
The LIL-Stat Protein Contains the Conserved P-tyr and P-tyr Binding Sites Found in Other Stat Proteins This example illustrates that the novel LIL-Stat protein contains both a phosphorylated tyrosine and a phosphorylated tyrosine binding function, both of which are essential for the binding of LIL-Stat to its recognition sequence. The LIL-Stat protein contains both a phospho-tyrosine binding domain and at least one phospho-tyrosine residue. EMSAs were conducted as in Example 1. Phospho-tyrosine (P-Tyr) was used at 0 to 25 mM and phospho-serine (P-Ser) and threonine (P-Thr) were used at 25 mM. The binding reactions used 1.5 μl of anti-phospho-tyrosine antibody (Upstate Biotechnology, Inc., Lake Placid, N.Y.). The results of these experiments were the abrogation of DNA binding by the anti-P-Tyr antibody. This demonstrated that the LIL-Stat protein, like other Stat family members, is tyrosine phosphorylated. In addition, these experiments demonstrated that phospho-tyrosine (P-Tyr), but not phosphoserine or threonine (P-Ser and P-Thr) can abrogate DNA binding, as has been reported for other Stat factors (Sadowski et al., Science 261:1739 (1993)). Phenyl phosphate also abrogated binding at similar concentrations. These results show that LIL-Stat possesses an essential SH2-like P-Tyr binding domain. Consequently, additional domains carboxyl to the conserved amino terminus found in all known Stat family members are likely present in LIL-Stat.

The data shows that IL-1, like many other cytokines, induces an immediate early (15 min in the absence of protein synthesis) tyrosine phosphorylated Stat factor.

Example 4
The Binding Sequence for the LIL-Stat Protein

This example illustrates a procedure for determining the involvement of nucleotides beyond the 9 nucleotides of the LIL-Stat binding sequence. A complementary 9 nucleotide long oligonucleotide pair representing the LIL-Stat binding site is synthesized using an automated oligonucleotide synthesizer. In addition, two longer oligonucleotide pairs containing an additional 5 base pairs on both sides of the LIL-Stat binding site are also synthesized. The 5 base pairs on each side (10 base pairs total) represent the flanking sequence contained within the IL-1β gene between positions −2854 and −2850, as well as between positions −2840 and −2835. One of the two longer oligonucleotides contains the native 9 base pair LIL-Stat binding site and the total of 10 base pairs of flanking sequence representing transversions (i.e., exchanging G with T and C with A) with respect to the native IL-1β sequence. The other longer oligonucleotide set contains the native 9 base pair LIL-Stat binding site with the 10 base pair flanking sequence representing transitions (i.e., exchanging G with A and C with T) with respect to the native IL-1β sequence. The three resulting double stranded oligonucleotides are radiolabeled at the 5' end using $\gamma$-$^{32}$P-labeled ATP and bacteriophage T4 polynucleotide kinase along with the native IL-1β gene sequence not containing any transversion or transition mutations. EMSA analysis employing a nuclear extract containing activated LIL-Stat (e.g., from IL-1β treated EL4 cells) is used to determine the level of LIL-Stat binding to the four probes. Equivalent binding of LIL-Stat to all four probes, or to the short 9 base pair long probe, demonstrates that only the 9 base pairs are necessary and sufficient for efficient recognition by LIL-Stat. This is because both conservative (transitions) and nonconservative (transversions) structural changes in the flanking sequence do not affect LIL-Stat binding.

Example 5
Identification of Agents Which Inhibit Interaction Between LIL-Stat Protein and Its DNA Binding Sequence Using an Electrophoretic Migration Shift Assay (EMSA)

This example illustrates a procedure for measuring whether or not a test agent inhibits interaction between LIL-Stat protein and a nucleic acid having a LIL-Stat binding sequence.

$10^8$ monocyte cells are cultured in the presence of 10 μg/ml of the stimulant lipopolysaccharide, E. coli serotype 055:B5 or any other competent serotype from E. coli or other bacterial strain, such as S. albus, for approximately 10 minutes. The test agent is added to the tissue culture medium. After 15 minutes, the cells are harvested and cellular nuclear extracts are prepared by modifications of previously published procedures (Shirakawa et al., Mol. Cell. Bio. 9:2424–2430 (1989); Dignam et al., Nucl. Acids Res. 11:1475–1489 (1983); Prywes et al., Cell 47:777–784 (1986)). The harvested cells are washed with phosphate buffered saline and incubated in 5 ml of Buffer A (10 mM HEPES, pH 7.9, 5 mM $MgCl_2$, 10 mM NaCl, 0.3M sucrose, 0.1 mM EGTA, 0.5 mM dithiothroitol (DTT), 0.5 mM phenylmethylsulfonyl fluoride (PMSF)) containing the following protease inhibitors (1 μg/ml final concentration for each): antipain, aprotinin, chymostatin, leupeptin, and pepstatin A, and the following phosphatase inhibitors: 1 mM $MnCl_2$, 1 mM sodium orthovanadate, 10 mM NaF, 5 mM sodium pyrophosphate, and 9 mM β-glycerophosphate. The EGTA, protease inhibitors, and phosphatase inhibitors are included in order to decrease spontaneous inactivation or overactivation of LIL-Stat due to activation of $Ca^{++}$ dependent kinases, proteolytic enzymes, and phosphatases. When compounds known to be capable of phosphatase action are tested in the assay, one or more of the phosphatase inhibitors is present at a reduced level in order to optimize the resultant effect.

For cell culture testing, the cells are centrifuged in Buffer A (see CNE Preparation above) and Dounce homogenized. The homogenate is then microcentrifuged for 30 sec, and nuclei resuspended in 0.8 ml of Buffer B either with or without protease and phosphatase inhibitors (20 mM HEPES, pH 7.9; 5 mM $MgCl_2$, 300 mM KCl, 0.2 mM EGTA; 25% glycerol; 5 mM DTT; 0.5 mM PMSF) and gently rocked on a platform at 4° C. for 30 min. After 30 min of microcentrifugation at 4° C., protein concentrations are measured using a Bio-Rad protein assay kit and supernatants frozen at −70° C. Similar results are obtained if perfused tissue or whole animals are used instead of cell cultures. For tissue sample testing, cells are disaggregated either mechanically or by trypsin treatment, washed in Buffer A and then Dounce homogenized as above for tissue culture cells. Disaggregated tissue cells can be maintained in culture, subjected to ex vivo treatments, and then processed in a manner identical to that of tissue culture cells.

A binding reaction is performed using these prepared cellular nuclear extracts. The total volume of the reaction is 15 $\mu$l and contains a total of 3 $\mu$g of protein derived from the above described cellular nuclear extract. 0.2 $\mu$g poly deoxyInosine•deoxyCytidine (poly dI•dC), 0.2 ng of radiolabeled double-stranded DNA probe having a LIL-Stat protein binding sequence (5,000 to 20,000 cpm), and 5 $\mu$l of 3X Binding Buffer (3XBB). For preparation of 50 ml of 3XBB, 1.5 ml Tris-HCl, pH 7.5, 6.0 ml 1M NaCl, 300 $\mu$l 0.5M $Na_2EDTA$, and 6 ml glycerol are mixed. Immediately prior to use, 1 $\mu$l 2-mercaptoethanol is added to 5 ml of 3XBB. The radiolabeled probe is generated by using DNA polymerase Klenow fragment and one to four different (A, T, G and C) $\alpha$-$^{32}$P-labeled deoxynucleotide triphosphates at 3,000 Ci/mmol. Alternatively, $\gamma$-$^{32}$P labeled ATP and bacteriophage T4 polynucleotide kinase can be used for non-recessed 5'-end dephosphorylated oligonucleotides. Oligonucleotides possessing 5' terminal phosphates are treated with calf intestinal phosphatase prior to treatment with kinase. Alternatively, E. coli alkaline phosphatase can be used. The DNA binding reaction is incubated for 30 min at room temperature.

The binding reaction is analyzed by polyacrylamide gel electrophoresis (PAGE) on a 0.5XTris-Borate-EDTA (0.5XTBE) buffered 4% polyacrylamide gel run at room temperature. Although this method describes TBE electrophoresis for EMSA, similar results are obtained if other buffer systems are used, e.g., Tris-Na Acetate-EDTA (TAE) (Shirakawa et al., Mol. Cell. Bio. 9:2424–2430 (1989)). Readout of results is accomplished by exposure to X-ray film or by direct radioactive detection, such as a phosphor imaging plate or other high energy beta particle detector. Resolution of EMSA by PAGE is done on a 4% polyacrylamide gel. The gel solution is: 20 ml 30% acrylamide bisacrylamide solution (29:1 ratio of acrylamide to bisacrylamide), 15 ml 5XTBE buffer, and water to 150 ml total volume. Polymerization for a 45 ml sample of the gel solution is initiated by the addition of 230 $\mu$l of a freshly prepared 10% aqueous solution of ammonium persulfate and 43 $\mu$l of TEMED). The solution is immediately poured into an appropriate electrophoresis device and polymerization is allowed to complete so as to result in a 1.5 mm thick, 14 cm long gel. Other gel dimensions also can be effectively used. After polymerization, the gel is pre-run for 1 hour at 100 V, 15 to 20 mA, in order to remove unpolymerized contaminants. The sample is then loaded and the gel is run for 2.5 hours under the same conditions as the pre-run. The electrophoresis is conducted at room temperature.

If the test agent inhibits interaction between LIL-Stat protein and its DNA binding sequence, then the gels show a decrease in the intensity of the LIL-Stat specific protein DNA complex. If the test agent is not such an inhibitor, then the gels show no change as compared to reference.

Those skilled in the art will be able to ascertain, using no more than routine experimentation, many equivalents of the specific embodiments of the invention described herein. These and all other equivalents are intended to be encompassed by the following claims.

What is claimed is:

1. A method of finding an agent which inhibits interaction between LIL-Stat protein and a nucleic acid having a LIL-Stat binding sequence where said LIL-Stat binding sequence is TTNCNNAGA (SEQ ID NO: 1), comprising:

contacting said LIL-Stat protein with said nucleic acid in the presence of an agent, it being unknown whether said agent inhibits or does not inhibit said interaction; and determining whether or not said agent inhibits said interaction of said LIL-Stat protein and said nucleic acid.

2. The method of claim 1 wherein said sequence comprises:

TTCCTGAGA (Sequence ID No. 2).

3. The method of claim 1 wherein said determining step is by an electrophoretic migration shift assay.

4. A method of screening for an agent which inhibits interaction between LIL-Stat protein and a nucleic acid having a LIL-Stat binding sequence where said LIL-Stat binding sequence is TTNCNNAGA (SEQ ID NO:1), comprising:

providing separately, test cells and reference cells, said test cells and said reference cells being the same type of cells;

treating said test cells and said reference cells with a stimulant;

treating said test cells with a test agent;

preparing a first nuclear extract from said test cells and a second nuclear extract from said reference cells;

contacting said first nuclear extract with a first nucleic acid having said LIL-Stat protein binding sequence and said second nuclear extract with a second nucleic acid having said LIL-Stat binding sequence, said first nucleic acid and second nucleic acid being the same type of nucleic acid;

comparing the binding between said first nuclear extract and said first nucleic acid and between said second nuclear extract and said second nucleic acid so as to determine the presence or absence of differential binding; and determining whether or not said test agent inhibits interaction between said LIL-Stat protein and said nucleic acid having said LIL-Stat binding sequence based upon the presence or absence of said differential binding.

5. The method of claim 4 wherein said test cells and said reference cells are selected from the group consisting of T cells, fibroblasts and monocytes.

6. The method of claim 4 wherein said stimulant is selected from the group consisting of lipopolysaccharide, IL-1 proteins, phorbol myristate acetate, cell adherents to glass, cell adherents to polystyrene, complement proteins, calcium ionophores, β-glucan polymers, and mixtures thereof.

7. The method of claim 4 wherein said stimulant is selected from the group consisting of lipopolysaccharide, IL-1 proteins, and mixtures thereof.

8. The method of claim 4 wherein said treating with said stimulant is done prior to said treating with said test agent.

9. The method of claim 4 wherein said treating with said stimulant is done subsequent to said treating with said test agent.

10. The method of claim 4 wherein said first nuclear extract and said second nuclear extract are further treated with a protease inhibitor.

11. The method of claim 4 wherein said first nuclear extract and said second nuclear extract are further treated with a phosphatase inhibitor.

12. The method of claim 4 wherein said binding is determined by an assay selected from the group consisting of an electrophoretic migration shift assay and a solid phase affinity assay.

13. The method of claim 4 wherein said test cells and said reference cells are obtained from a cell culture, a perfused tissue, or an animal.

14. A method of screening for an agent which inhibits interaction between LIL-Stat protein and a nucleic acid having a LIL-Stat binding sequence where said LIL-Stat binding sequence is TTNCNNAGA (SEQ ID NO:1), comprising:

providing cells;

treating said cells with a stimulant;

treating said cells with a test agent;

preparing a nuclear extract from said cells;

contacting said nuclear extract with said nucleic acid having a LIL-Stat protein binding sequence;

determining the binding between LIL-Stat protein, from said nuclear extract, and said nucleic acid; and identifying said agent by a reduction in said binding compared to cells that have been identically treated except that no test agent has been added.

15. A method of finding an agent which inhibits interaction between LIL-Stat protein and a nucleic acid having a LIL-Stat binding sequence where said LIL-Stat binding sequence is TTNCNNAGA (SEQ ID NO:1), comprising:

contacting a predetermined cell extract with an agent, it being unknown whether said agent inhibits or does not inhibit said interaction, utilizing a stimulant which enables LIL-Stat protein production; and determining whether or not said agent inhibits said interaction of said LIL-Stat protein and said nucleic acid.

* * * * *